(12) United States Patent
Gittleman et al.

(10) Patent No.: US 9,265,591 B1
(45) Date of Patent: Feb. 23, 2016

(54) DENTAL PROSTHESIS ALIGNMENT APPARATUS

(71) Applicants: Neal B. Gittleman, Houston, TX (US);
Daniel Jay Schacht, Houston, TX (US)

(72) Inventors: Neal B. Gittleman, Houston, TX (US);
Daniel Jay Schacht, Houston, TX (US)

( * ) Notice: Subject to any disclaimer, the term of this patent is extended or adjusted under 35 U.S.C. 154(b) by 0 days.

(21) Appl. No.: 14/087,241

(22) Filed: Nov. 22, 2013

(51) Int. Cl.
*A61C 8/00* (2006.01)
*A61C 1/08* (2006.01)

(52) U.S. Cl.
CPC ............... *A61C 8/0053* (2013.01); *A61C 1/084* (2013.01); *A61C 8/005* (2013.01); *A61C 8/0089* (2013.01)

(58) Field of Classification Search
CPC ........ A61C 8/00; A61C 8/001; A61C 8/0048; A61C 8/005; A61C 8/0053; A61C 8/0054; A61C 8/0057; A61C 8/0059; A61C 8/0063; A61C 8/0065; A61C 8/0068; A61C 8/0069; A61C 1/084; A61C 8/0089

USPC ................ 433/167, 172, 173, 174, 177, 196, 433/201.1
See application file for complete search history.

(56) References Cited

U.S. PATENT DOCUMENTS

| | | | | |
|---|---|---|---|---|
| 4,575,340 A | * | 3/1986 | Lustig | 433/173 |
| 4,681,542 A | * | 7/1987 | Baum | 433/172 |
| 4,836,196 A | * | 6/1989 | Park et al. | 606/246 |
| 4,842,518 A | * | 6/1989 | Linkow et al. | 433/174 |
| 5,571,016 A | * | 11/1996 | Ingber et al. | 433/173 |
| 5,848,897 A | * | 12/1998 | Jansen | 433/182 |
| 2008/0241790 A1 | * | 10/2008 | Gittleman | 433/174 |
| 2012/0214130 A1 | * | 8/2012 | Krivoruk | 433/173 |

* cited by examiner

*Primary Examiner* — Edward Moran

(57) ABSTRACT

A dental prosthetic alignment mechanism that simultaneously corrects all vertical, parallel and angular misalignments between several abutments and their matching substructure coping sleeves suitable for a multi-implant prosthesis. Upon tightening the abutment retaining screw cylindrical segments are forced outward and into locking alignment with the angled or misaligned coping sleeve without the need for additional laboratory procedures such as cutting and welding to correct the undercase.

1 Claim, 5 Drawing Sheets

DENTAL PROSTHESIS ALIGNMENT APPARATUS

BACKGROUND OF THE INVENTION

Figure 1:
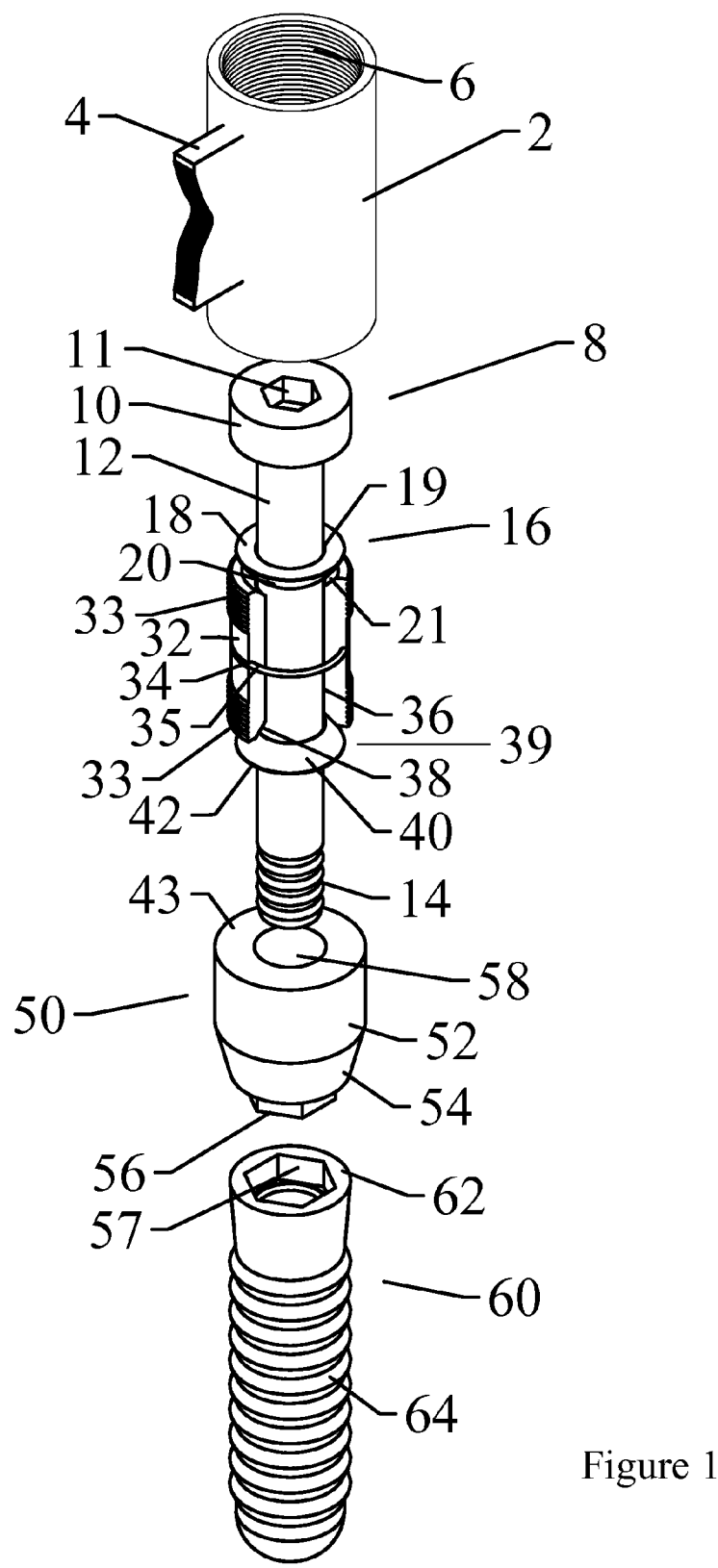

Modern dental practices, seeking economies of time at the patient's side and in the laboratory, tend to provide completed and installed implant prosthesis in as few as a single sitting. Three-dimensional images displayed and manipulated on a computer screen are derived from a CAT scan (Computer Aided Tomography) of all oral structures. Virtual implants and prosthetics are tried in this virtual space until a best case is developed. The number and type of implants, their placement angles and depths, the density of bone and the avoidance of critical structures are tested in this virtual space. Surgical drilling and implant registration guides are generated with Rapid Prototyping tools to insure an almost exact relative placement of a set of implants.

Nonetheless, minor deviations and anatomical requirements can prevent the parallel alignment of implants and the matching abutments with the final prosthesis. Under these circumstances, additional laboratory procedures such as cutting and welding to correct the undercase must be done to fit the prosthesis. One solution suggested is to provide an abutment having a smaller mating end resulting in a gap between the abutment and prosthesis for cementing, referred to as the CAL technique. In the CAL technique, a disposable shim is slipped between each abutment and substructure sleeve to make a gap to compensate for misalignment.

Izador Brajnovic in U.S. Pat. No. 7,175,434 teaches an expandable cylinder to fill the gap between the distal end of the abutment and the substructure sleeve of the undercase of the prosthesis. This is a partial solution still requiring parallel placement of abutments. Charles D. Kownacki in U.S. Pat. No. 5,302,125 offers a ball-in-socket adjustment within the upper end of the implant, leaving the distal end of abutment unmodified. This offers compensation for angular misalignment without addressing parallel displacement or vertical discrepancies of the abutments. The Kownacki placement of the ball-in-socket below the soft tissue invites bacteria and can compromise good oral hygiene.

FEATURES OF THE INVENTION

The current invention addresses both the parallel and angular displacement of the axis between abutments with the same mechanism. The apparatus resides above the soft tissue and avoids oral hygiene and adjustment difficulties. This apparatus works equally well with prosthetics built with standard laboratory techniques. This invention solves the last sub-millimeter misalignment problem.

The avoidance of peri-implant bone loss and soft tissue inflammation requires an unstressed fit along with a smooth transition through the soft tissue.

In the embodiment of this invention, several degrees of freedom of motion for near perfect alignment are incorporated in a simple to install and adjust apparatus. Laboratory reworking and chair-side adjustments are reduced substantially or eliminated entirely.

The apparatus relies upon two sets of working surfaces to align cylindrical segments within a coping sleeve. Each set of working surfaces consists of a hemispherical surface riding upon a conical surface to compensate for misalignment. Upon tightening a central screw, the cylindrical segments are forced outward into alignment with the angled or misaligned coping sleeve.

A BRIEF DESCRIPTION OF THE DRAWINGS

Figure 2:
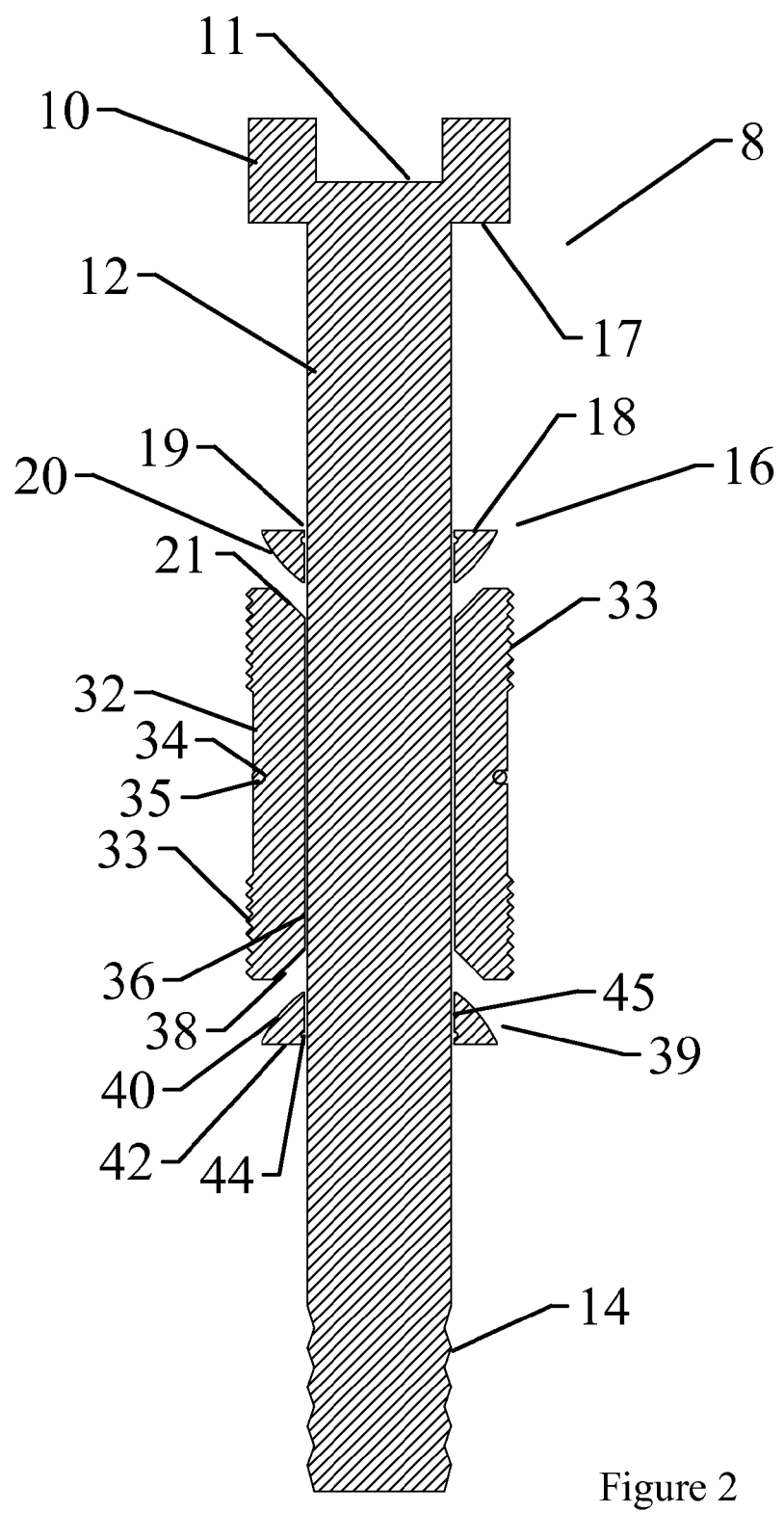
Figure 3:
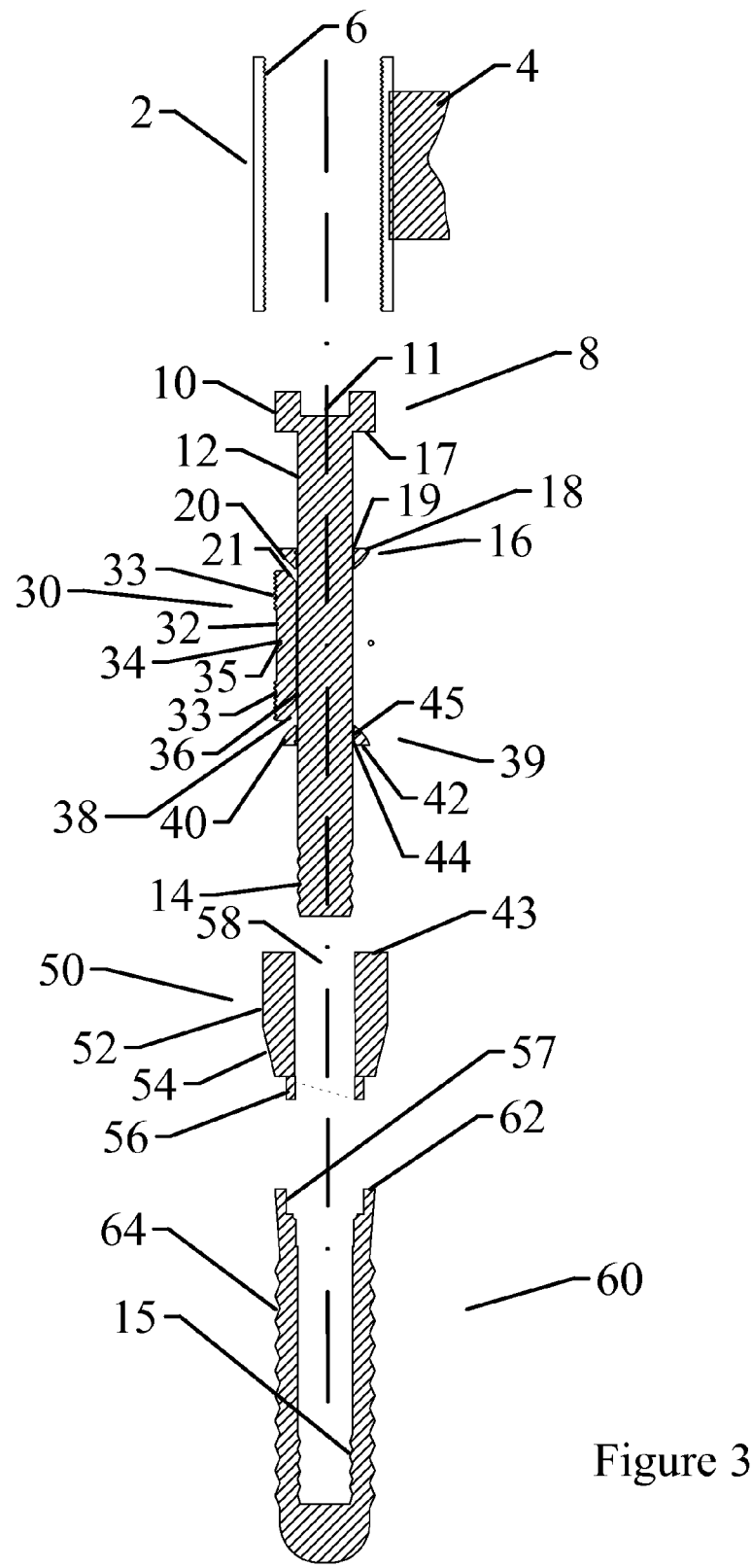
Figure 4:
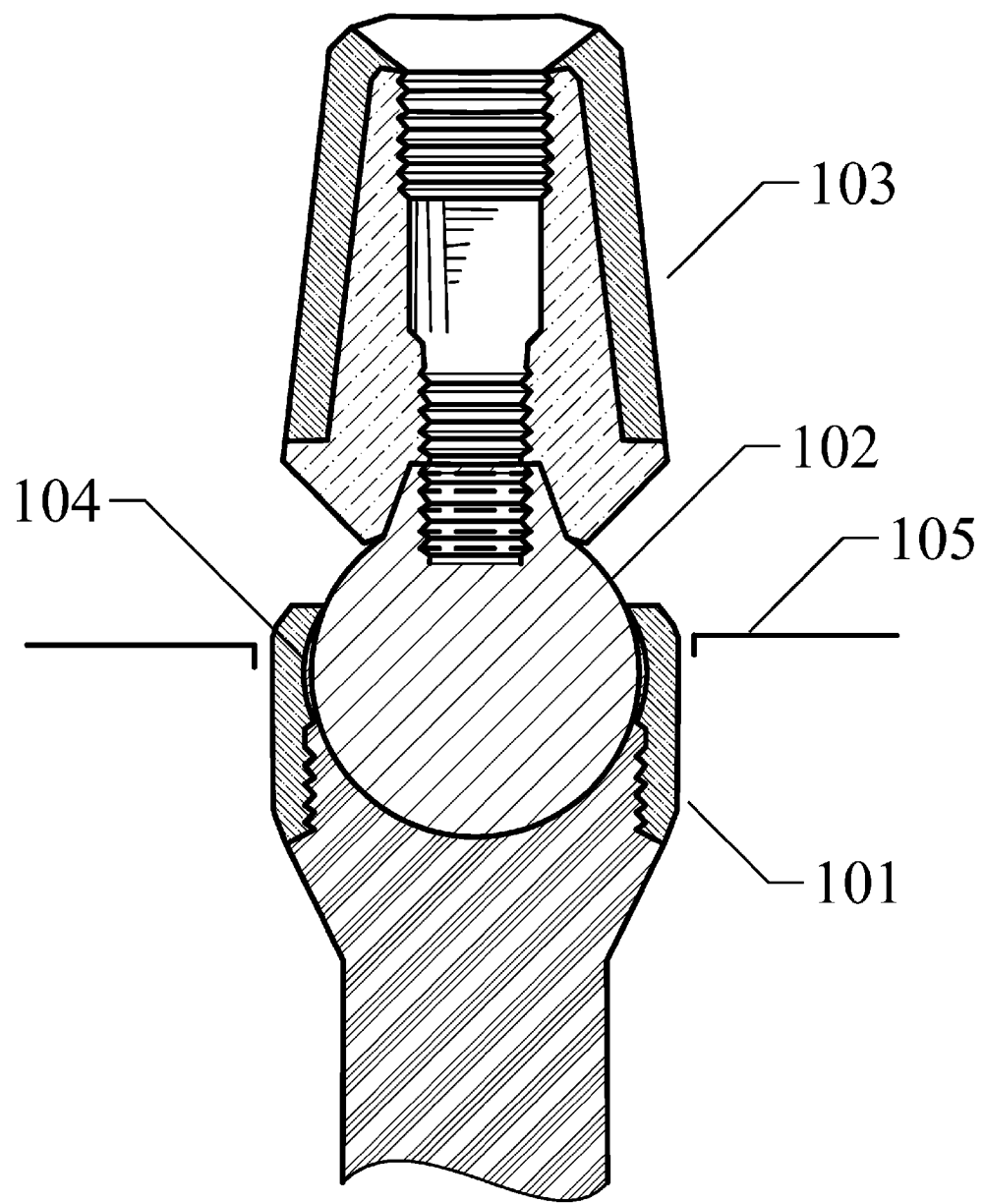
Figure 5:
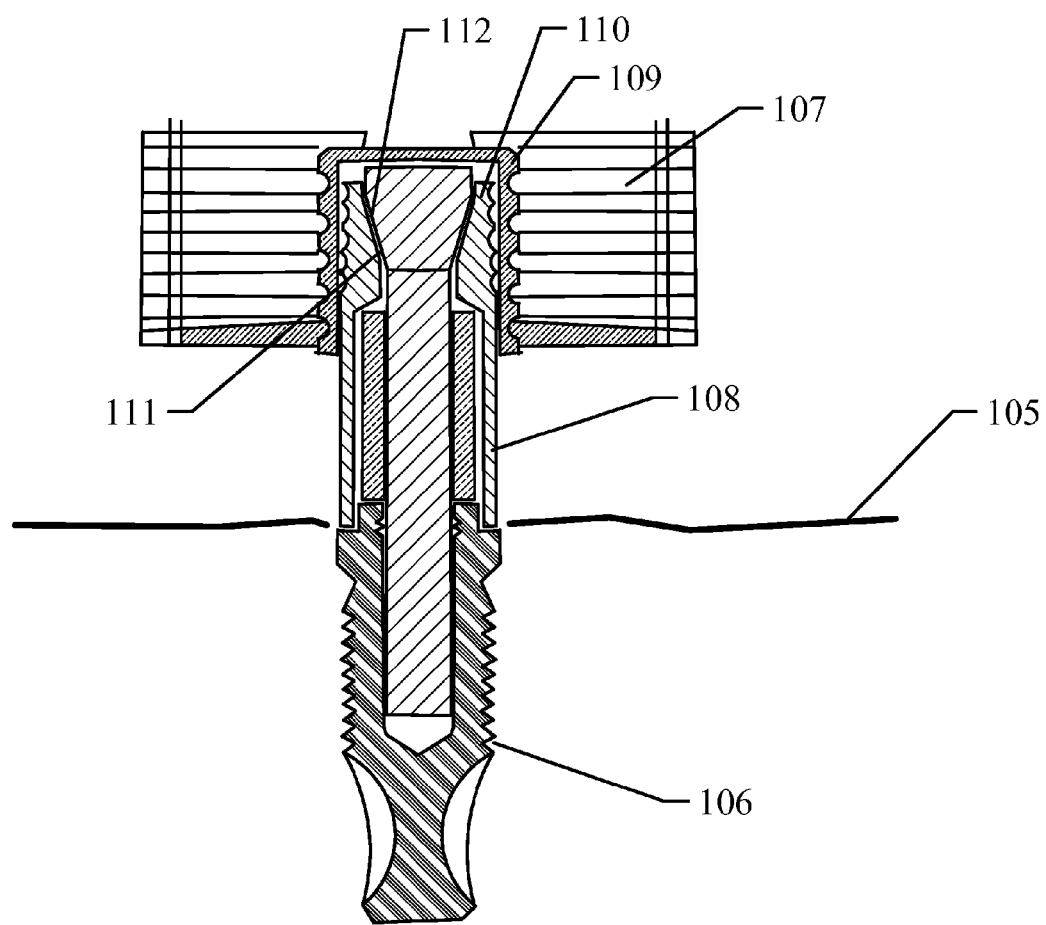

FIG. 1 is an exploded view of the adjustment apparatus;
FIG. 2 is cross sectional view of elements of the adjustable locking apparatus;
FIG. 3a is an cross sectional view of the apparatus with the substructure sleeve and implant adjustments;
FIG. 4 is a prior art cross sectional schematic view of a ball-in socket assembly located below the gum line; and
FIG. 5 is a prior art cross sectional schematic view of a cylindrical expansion abutment;

A DETAILED DESCRIPTION OF THE DRAWINGS

As detailed in FIG. 1, a vertically exploded view of the coping 2 slips easily over screw 8, upper washer 16, cylindrical segments 32, and lower washer 39. Bridging element 4 is connected to other copings of the prosthesis. The screw threads 14 extend through abutment 50 to mate with implant fixture 60 internal threads 15 (FIG. 3). Screw head 10 has driving means 11 known to the art. Resilient elastomeric band or o-ring 35 in groove 34 hold the segments 32 in close proximity to ease insertion within coping 2. Three segments are optimum. One of the segments is not shown for clarity. Internal grooves 6 lock with external ridges 33 upon tightening the screw 8. The screw extends through the abutment 50 into implant fixture 60.

Alignment of the cylindrical segments within a skewed coping are accomplished in the following manner as illustrated in FIGS. 2 and 3:

Upper washer 16 with gap 19 rides loosely upon the shaft 12 of the screw 8.

Upper flat 18 slides while mating with flat underside 17 of the screw.

Lower hemispherical surface 20 of the upper washer mates with cylindrical surfaces 21 of the segments 32.

Likewise, lower conical surfaces 38 of segments 32 slides while mating with upper hemispherical surface 40 of lower washer 39.

Flat lower surface 42 of the lower washer 39 slides while mating with flat surface 43 of the abutment. Gap 19 on the upper washer and gap 45 on the lower washer allow for lateral misalignment between the coping and the centerline axis of the implant fixture.

Angular misalignment is repaired by the interaction of the sliding contact between surfaces 20 and 21 in combination with surfaces 38 and 40.

An internal groove 44 in the lower washer retains an o-ring or elastomeric material (46) to hold the lower washer on the screw shaft to retain all elements. Elastomeric retainer 35 in groove 34 surrounding cylindrical segments 32 hold the segments in close proximity to the screw shaft for easy insertion into the coping.

Ridged grooves in the circumferential grooved pattern 6 in the coping and ridged projections 33 on the cylindrical segments removably lock together within a fraction of a millimeter upon tightening the screw. No permanent distortion of or deformation of any surface occurs. All elements are removable and reusable.

FIG. 3 shows a standard abutment 50 having a through hole 58 an outer surface 52 and 54 with a lower clocked projection 56 to mate with recess 57 in the implant fixture 60. Alternately, the abutment may be dispensed with in certain circumstances. In that case lower washer surface 42 rides directly upon upper flat surface 62 of the implant fixture.

As the drawings illustrate, the combined action of both the upper and lower spherical/conical sliding surfaces and the combined sliding action between the flats on both upper and lower washers and their respective mating surfaces are needed to anticipate any angular and lateral misalignment. If any of these motional innovations are absent, the cylindrical segments will not uniformly lock within the coping sleeve. Tissue damaging stresses will be placed on the implant fixtures and overcase structure.

In FIG. 4 (Kownacki U.S. Pat. No. 5,302,125), cited as prior art, an implant 101 and abutment 103 are shown with the soft tissue line 105 approximating where the underlying adjustment is located. The ball assembly 102 is held in place by tightening a cap-like structure 104. The current invention offers a substantial improvement by avoiding the soft tissue while making compensating adjustments. Hygiene is compromised in the prior art.

Furthermore, alignment is only possible in an arc centering on the midpoint of the ball. Adjustments for parallel displacement are not possible. Adjustment in the vertical placement of a substructure sleeve is not possible with this prior art.

Likewise, the prior art in FIG. 5 (Brajnovic U.S. Pat. No. 7,175,434) teaches an implant 106 located below the soft tissue line 105 with an abutment 108 having a cylindrical expanding head 110. The expanding head of the cylindrical abutment slides within the substructure sleeve 109 of the bridge assembly 107. The wedge-like portion of the screw head 111 bears against the inner surface of the abutment expanding head at 112 to lock the abutment within the substructure sleeve. The adjustment is along the vertical axis of the implant only. No offset or angular displacement is compensated by this prior art design. If off-centered, the expansion head of this design does not bear against the inner wall of the substructure sleeve with equal force around the complete inner circumference. This places a lateral strain upon the implant. Thus, this prior art relies upon a non-reversible permanent distortion of the substructure sleeve or the securing screw to achieve a true lock. The current invention, by centering the locking mechanism, applies equal forces without permanent distortion of the sleeve, while adjusting for lateral, angular and vertical misalignment. This allows for the reversible removal by loosening the locking screw. The elements of the apparatus, consisting of the coping, the mounting screw, upper washer, locking cylindrical segments, cylinder o-ring, lower washer, and retaining o-ring are pre-assembled in a kit for ease of placement in packaging suitable for sterilization.

Each apparatus is placed and loosely screwed into each implant. The prosthesis substructure coping sleeves are centered over each locking assembly. The screws are tightened in the preferred sequence.

Where it is understood that the locking assembly is primary applicable to the field of implant dentistry, consideration should be given to equal use in anchoring any medical prosthesis or device within a cylindrical bore in bone or firm body structure.

What is claimed is:

1. A dental apparatus for aligning and locking an implant assembly comprising:

an overcase coping comprising horizontal circumferential grooves and projections on the upper and lower inner surfaces;

a mounting screw having a shaft and a head with a flat undersurface;

an upper washer having a flat upper surface and a hemispherical lower surface;

an at least two cylindrical segments having a concave internal conical upper and a concave internal conical lower surface;

the at least two cylindrical segments having horizontal circumferential grooves and projections on the upper and lower outer surfaces to mate with and lock within the horizontal circumferential grooves and projections on the inner surface of the overcase coping, to maintain a required vertical spacing;

a retaining elastomeric band surrounding and residing within a horizontal circumferential groove in the outer surface of the at least two cylindrical segments sited between the upper and lower horizontal circumferential grooves and projections, thereby holding the at least two cylindrical segments together substantially in the form of a cylinder;

a lower washer having a hemispherical upper surface and a flat lower surface;

the lower washer having a parts retaining elastomeric insert conforming to the shaft of the mounting screw;

wherein the screw head flat undersurface slides while mating with the flat upper surface of the upper washer;

wherein the hemispherical lower surface of the upper washer slides while mating with the concave internal conical upper surface of the at least two cylindrical segments;

wherein the hemispherical upper surface of the lower washer slides while mating with the lower concave internal conical surface of the at least two cylindrical segments;

wherein the flat lower surface of the lower washer slides while mating with a flat upper surface of an abutment;

thereby, removeably locking the coping and the abutment upon tightening the screw while adjusting for lateral, vertical and angular misalignment.

\* \* \* \* \*